(12) United States Patent
Henck et al.

(10) Patent No.: US 8,389,778 B2
(45) Date of Patent: Mar. 5, 2013

(54) PREPARATION OF MANNITOL MODIFICATION III

(75) Inventors: Jan-Olav Henck, West Lafayette, IN (US); Mark C. Andres, West Lafayette, IN (US); Linda J. McCausland, West Lafayette, IN (US)

(73) Assignee: Aptuit (West Lafayette), LLC, West Lafayette, IN (US)

( * ) Notice: Subject to any disclaimer, the term of this patent is extended or adjusted under 35 U.S.C. 154(b) by 275 days.

(21) Appl. No.: 12/601,270

(22) PCT Filed: May 21, 2008

(86) PCT No.: PCT/US2008/064362
§ 371 (c)(1),
(2), (4) Date: Sep. 17, 2010

(87) PCT Pub. No.: WO2008/147811
PCT Pub. Date: Dec. 4, 2008

(65) Prior Publication Data
US 2011/0065967 A1 Mar. 17, 2011

Related U.S. Application Data

(60) Provisional application No. 60/939,389, filed on May 22, 2007.

(51) Int. Cl.
*C07C 29/78* (2006.01)
*C07C 29/94* (2006.01)
(52) U.S. Cl. .................. 568/868; 568/853; 568/854
(58) Field of Classification Search .................. None
See application file for complete search history.

(56) References Cited

U.S. PATENT DOCUMENTS

| 3,632,656 A | | 1/1972 | Unver |
| 3,864,406 A | * | 2/1975 | Melaja et al. ............ 568/872 |
| 4,670,611 A | * | 6/1987 | Lemay ............... 127/60 |
| 5,023,092 A | * | 6/1991 | DuRoss ............ 426/3 |
| 6,235,947 B1 | * | 5/2001 | Yoshinari et al. ......... 568/852 |
| 6,503,918 B2 | * | 1/2003 | Yoshinari et al. ......... 514/277 |
| 2001/0001106 A1 | * | 5/2001 | Yoshinari et al. ......... 568/852 |

FOREIGN PATENT DOCUMENTS

| AU | 3215771 A | 2/1973 |
| AU | 3771172 A | 7/1973 |
| DE | 10063973 A1 | 6/2002 |
| WO | 2008147811 A1 | 12/2008 |

OTHER PUBLICATIONS

Debord et al., Drug Development and Industrial Pharmacy (1987), 13(9-11), p. 1533-1546.*
Burger et al., Journal of Pharmaceutical Sciences (2000), 89(4), p. 457-468.*
Becker, Z. Phys. 14:369 (1923).
Berman et al., "The Crystal Structures of the α' and β Forms of D-Mannitol," Acta Cryst. B 24:442-449 (1968).
Fronczek et al., "Three polymorphs (α, β, and δ) of D-mannitol at 100 K," Acta Cryst. C 59:567-570 (2003).
Joiris et al., "The compression behaviour of orthorhombic paracetamol," Pharm. Res. 15(7):1122-1130 (1998).
Kaminsky et al., "Crystal optics of Mannitol, C6H14O6: Crystal growth, structure, basic physical properties, birefringence, optical activity, Faraday effect, electro-optic related effect and model calculations," Z. Kristallogr. 212:283-296 (1997).
Walter-Levy, "Sur les variétés cristallines du D-mannitol," Acad. Sci., Ser. C 267:1779-1782 (1968) (Abstract).
Yu et al., "Existence of a Mannitol Hydrate during Freeze-Drying and Practical Implications," J. Pharm. Sci. 88:196-198 (1999).
International Search Report for PCT/US2008/064362 dated Aug. 22, 2008.
International Preliminary Report on Patentability and Written Opinion of the International Searching Authority for PCT/US2008/064362 dated Nov. 24, 2009.

* cited by examiner

*Primary Examiner* — Brian J Davis
(74) *Attorney, Agent, or Firm* — J.A. Lindeman & Co., PLLC

(57) ABSTRACT

Methods for preparing mannitol modification III are described herein. The methods relate to preparing solutions of mannitol in a suitable solvent and an auxiliary agent and solidifying from the solutions mannitol of modification III.

18 Claims, 5 Drawing Sheets

PREPARATION OF MANNITOL MODIFICATION III

CROSS REFERENCE TO RELATED APPLICATIONS

This is a National Phase Application in the United States of International Patent Application No. PCT/US2008/064362 filed May 21,2008, which claims priority under 35U.S.C. §119 to U.S. Provisional Application Ser. No. 60/939,389, filed May 22, 2007, which is incorporated herein by reference.

FIELD OF THE INVENTION

The invention relates generally to the production of mannitol and more specifically to the production of mannitol modification III.

BACKGROUND

The acyclic sugar alcohol mannitol, shown below, is an excipient commonly used in the pharmaceutical formulation of tablets, granulated powders for oral use, and as a stabilizer in protein formulations. Mannitol is generally described to be non-hygroscopic.

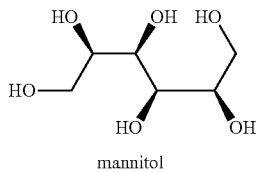 [SMILES: OC[C@@H](O)[C@@H](O)[C@H](O)[C@H](O)CO]

mannitol

Three polymorphic crystal forms (A. Burger et al. *J. Pharm. Sci.* 2000, 89, 457) and a hemihydrate (L. Yu et al. *Pharm. Sci.* 1999, 88, 196) of mannitol are described in the literature. The term "modification" as used herein refers to one of the three polymorphic crystal forms. By "polymorphic" what is meant is that mannitol is known to crystallize into one of at least three different solid-state structures. Each structure exhibits different solid-state properties such as dissolution, hygroscopicity, and compression properties. For example modification I (β-mannitol, I) is the thermodynamically stable crystal form under ambient conditions. Modification II (α-mannitol, II) and modification III (δ-mannitol, III) are thermodynamically metastable under ambient conditions, but can be crystallized in large quantities and are durable. In one report, for example, modification III did not transform into modification I over a period of 5 years if kept dry (A. Burger et al. *J. Pharm. Sci.* 2000, 89, 457). The physical properties such as melting points, enthalpies of fusion, vibrational spectra and densities are described in the scientific literature (A. Burger et al *J. Pharm. Sci* 2000, 89, 457). Mannitol hemihydrate was observed during lyophilization of aqueous solutions of mannitol. However, the hemihydrate is unstable under ambient conditions. Single crystal X-ray structures have been reported for modifications I: (a) Berman et at. Acta Cryst. B 1968, 24, 442; b) Walter-Levy C. R. *Acad. Sci., Ser. C* 1968, 267, 1779; c) Kaminsky et al. *Z. Krystallogr.* 1997, 212, 283; d) Fronczek et al. *Acta Cryst. C* 2003, 59, 567), II (a) Walter-Levy C. R. *Acad. Sci., Ser. C* 1968, 267, 1779; b) Fronczek et al. *Acta Cryst. C* 2003, 59, 0567), and III (a) Walter-Levy C. R. *Acad Sci., Ser. C* 1968, 267,1779; b) Backer Z. *Phys.* 1923, 14, 369; c) Fronczek et al. *Acta Cryst. C* 2003, 59, o567). A crystal structure solution from powder was published for the hemihydrate and also for modification III.

One feature of an excipient is its ability to compress during the formation of a tablet. For example, paracetamol (Joiris et al. *Pharm. Res.* 1998, 15, 1122) exists in multiple crystalline forms including the thermodynamically stable crystal form (monoclinic form) and a metastable form which is orthorhombic. The monoclinic form cannot be compressed directly which is why paracetamol tablets are usually produced through a wet granulation process. The metastable orthorhombic crystal form of paracetamol, however, can be compressed directly without having to go through the additional wet granulation processing required by the monoclinic form. Thus, by avoiding a wet granulation process, the orthorhombic form is less expensive and quicker to process.

Likewise, the compression properties of the crystal forms of mannitol differ from each other (A. Burger et al. *J. Pharm. Sci.* 2000, 89, 457). The compressibility of a material is its ability to be reduced in volume as a result of an applied pressure. Mannitol modification III exhibits the best compressibility followed by modification I and II (A. Burger et al. *J. Pharm. Sci.* 2000, 89, 457). Additionally, modification III shows better compactibility and friction of compacts (tablets) when compared with modifications I and II. The compactibility of a material is its ability to produce compacts with sufficient strength (hardness, friability) under the effect of densification. The friction of the compacts is usually determined by measuring the ejection force that is necessary to eject a compact (tablet) out of the tabletting machine as a function of the compression pressure that is needed to form the compact (tablet). Hence, modification III shows the best direct compression properties among the three anhydrous forms (A. Burger et al. *J. Pharm. Sci.* 2000, 89, 457). Currently, the majority of mannitol produced for pharmaceutical use is the thermodynamically stable modification I. In spray-dried products, mannitol usually exists as mixtures of modifications I and II.

Although the formation of mannitol modification III is known, for commercial production, it occurs as a byproduct of D-sorbitol production, which involves catalytic hydrogenation of glucose and/or fructose. In this commercial process, the mannitol is separated from the D-sorbitol by fractional crystallization. Mannitol modification III results because D-sorbitol inhibits the phase transformation of modification III into a thermodynamically more stable crystal form. The amounts of mannitol modification III produced as a by-product of sorbitol production often contain impurities and the quantities produced are insufficient to meet currently commercial demands. Alternatively, small amounts of mannitol modification III may be made by rapidly cooling an aqueous solution of mannitol to 0° C. and rapidly isolating the resulting solid before modification III reverts to modification I or II (A. Burger et al. *J. Pharm. Sci.* 2000, 89, 457). This process however, cannot be scaled up to produce commercially useful amounts of mannitol modification III.

Thus, modification III has been produced as a byproduct of sorbitol production but has not been made by direct crystallization methods. It should also be appreciated that the current demand for mannitol modification III is greater than the amount that may be produced by the current commercial method described above.

It would be advantageous, therefore, to have a method for making modification III of mannitol separate from the production of sorbitol. It would also be advantageous if the method could make commercially useful amounts of mannitol modification III.

SUMMARY OF THE INVENTION

In one aspect of the invention, a method for preparing mannitol modification III is provided comprising preparing a solution comprising mannitol, a suitable solvent, and an auxiliary agent and solidifying mannitol modification III from the solution.

In another aspect of the invention, an industrial scale method for preparing mannitol modification III is provided comprising preparing a solution comprising mannitol, a suitable solvent, and an auxiliary agent and solidifying mannitol modification III from the solution.

DETAILED DESCRIPTION OF THE INVENTION

Figure 1:
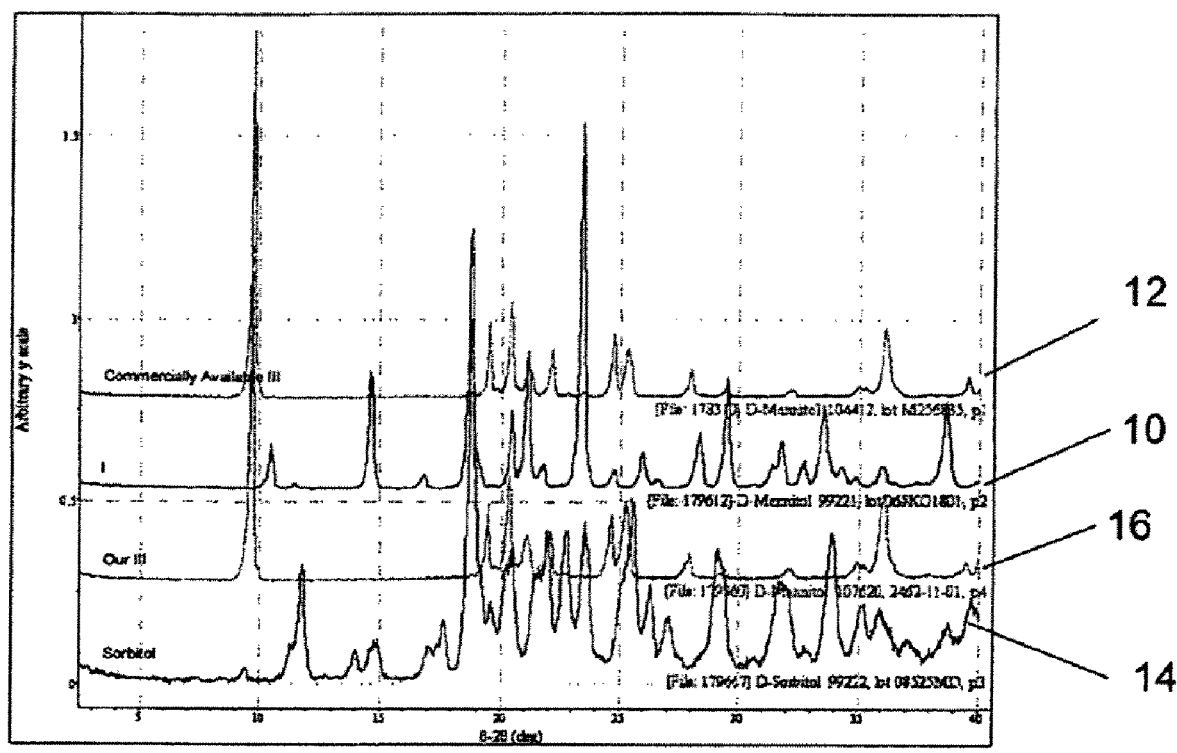
FIG. 1 is an x-ray powder diffraction pattern showing the diffraction patterns for sorbitol, mannitol modification I, commercially available mannitol modification III and mannitol modification III produced by the method of the present invention with sorbitol as the auxiliary agent.

Broadly, the invention provides a method for making mannitol modification III comprising solidifying mannitol modification III from solution. The mannitol modification III may be isolated from a solution where the solution comprises mannitol and at least one auxiliary agent dissolved in a suitable solution. In an exemplary embodiment, the mannitol modification III isolated from the solution is substantially pure. Substantially pure may be defined as from about 90% to about 100% pure.

In one embodiment of the invention, mannitol may be selected from modifications I, II, III, or the hemihydrate form, or a combination thereof, and may be dissolved in a suitable solvent, such as water, to form a solution. Examples of suitable solvents include water, acetone or any solvent in which mannitol is soluble.

An auxiliary agent is also added to the solution. By "auxiliary agent" what is meant is a chemical compound that is more soluble than mannitol in the suitable solvent and remains in solution when the mannitol modification III solidifies out. Additionally, when mannitol is solidified in the presence of an auxiliary agent, at least some of modification III is formed. Examples of auxiliary agents may include, but not be limited to, sorbitol, citric acid, glycolic acid, fructose, mannose, inorganic salts, (e.g. sodium chloride, potassium chloride, potassium nitrate, calcium chloride, etc.), or combinations thereof. While not wishing to be bound by theory, modification III may have the most favorable local minimum energy and therefore, be formed first. The auxiliary agent may inhibit the phase transition of modification III to the modifications I and II, which may have the more favorable global minimum energy.

It will be appreciated that there is no required order of addition of mannitol and the auxiliary agent to the solvent or the solvent to the mannitol and/or auxiliary agent. They may be added separately in any order, added in alternating amounts of each or added simultaneously.

Mannitol may be solidified, such as by crystallization, from a solution comprising mannitol, a suitable solvent, and an auxiliary agent to obtain modification III. Solidification of mannitol modification III may be achieved by a number of different techniques. In one embodiment of the invention, mannitol modification III may be solidified by cooling the solution comprising mannitol, a solvent, and an auxiliary agent. Other solidification techniques include evaporation, the addition of an anti-solvent, thermomicroscopy, crash cooling of the solution or a combination thereof.

Examples of conditions for methods of the invention are given in Example 1, Tables 1 and 2. The temperature of the solvent/solution was increased to from about 40° C. to about 60° C. to aid in the dissolution of the mannitol and/or auxiliary agent ($T_{in}$). While not necessary, the increased temperature may allow for more solids to be loaded in the solution and/or for decreasing the time needed to dissolve all solids added. In an exemplary embodiment, mannitol modification III may be solidified out of solution at a temperature of less than about 30° C. In an alternate exemplary embodiment, mannitol modification III may be solidified out of solution in a temperature range of from about 0° C. to about 45° C. ($T_{out}$). While these ranges are provided as an exemplary embodiment, it is contemplated that both $T_{in}$ and $T_{out}$ will vary depending on the solids loading and the auxiliary agent. It is well within the skill of those in the art, using these ranges as a guideline, to determine the optimal $T_{in}$ and $T_{out}$ without undue experimentation. Cooling of the solution need not be rapid and the solution can remain at the cooling temperature until the desired amount of solid modification III is obtained. It will be appreciated that, the greater the amount solids loading in solution, particularly of mannitol, the greater the amount of solid modification III that may solidify, at higher cooling temperatures and/or in shorter time frames. This is in contrast to previous methods of solidifying modification III from an aqueous solution with required the rapid cooling of the solution to 0° C. and then quickly filtering out the solid. In most of the examples of Tables 1 and 2, mannitol modification III was solidified from solution at temperatures above ambient temperature with the method of the invention. Tables 1 & 2 moved to Example 1.

The concentration of auxiliary agent used may vary with respect to the concentration of mannitol. When mannitol and the auxiliary agent are being added to solution independently, it may be advantageous to have a minimal amount of auxiliary agent. Alternatively, if the source of mannitol is a by-product of a fermentation process such as, but not limited to, corn by-products the molar concentration of auxiliary agent may be about the same as the concentration of mannitol. In an exemplary embodiment of the invention the concentration of the auxiliary agent may range from about 0.1 to about 1.0 g/mL. While this range is given for general guidance, the concentration of auxiliary agent is not contemplated to be bound by this range. It is well within the skill of those in the art to determine the amount of auxiliary agent required for the specific conditions used. In an exemplary embodiment, the ratio of auxiliary agent to mannitol may be, but not limited to, from about 1:10 to about 10:1 (mol/mol). In an exemplary embodiment, the ratio of auxiliary agent to mannitol is from about 1:2 to 2:1 (mol/mol). In an alternate exemplary embodiment, the amount of auxiliary agent may be from about 0.25 to about 0.4 g/ml in a solution with a total solids loading of from about 0.6 g/ml to about 0.9 g/ml.

The concentration of the auxiliary agent with respect to the concentration of mannitol may also be related to the solubility of the auxiliary agent with respect to the mannitol. For example, if the auxiliary agent has a significantly higher solubility than mannitol, more auxiliary agent may be added than when the auxiliary has a solubility closer to that of mannitol.

The different modifications of mannitol can be readily differentiated by their x-ray powder diffractograms. The Bruger reference (A. Burger et al. *J. Pharm. ScL* 2000, 89, 457) provides reference diffractograms as well as other parameters to distinguish mannitol modifications I, II and III from each other. FIG. 1 illustrates the powder x-ray diffraction patterns obtained from commercially obtained mannitol modification I (10), mannitol modification III (12) and sorbitol (14). As shown in FIG. 1, modification III (12) is clearly distinguishable from modification I (10). For example, the pattern corresponding to mannitol modification III possesses a characteristic peak at about 9.8 degrees two theta, which is absent from the other modifications of mannitol as well as from the hemihydrate. The characteristic peak at about 9.8 degrees two theta is also distinguishable over the auxiliary agent sorbitol. If another auxiliary agent in used that has peaks in the same region that would make it difficult to distinguish the formation of mannitol modification III, then another peak may be chosen such as, but not limited to, the peak at about 19.4 degrees two theta, which is also unique to modification III with regard to modification I (FIG. 1).

In addition, modification III of mannitol has a different diffraction pattern that the auxiliary agents. For example, as shown in FIG. 1, the diffraction pattern for sorbitol (14), as the auxiliary agent, is clearly distinguishable from mannitol modifications I (10) and III (12). The x-ray diffraction patterns corresponding to D-Glucose, glycolic acid, citric acid (hydrate), fructose, mannose, and sodium chloride are also distinguishable from the pattern for mannitol modification III. Because each solid-state material has a unique x-ray powder diffraction pattern, one can readily identify and distinguish modification III of mannitol from any other form of mannitol and from any of the auxiliary agents.

Figure 2:
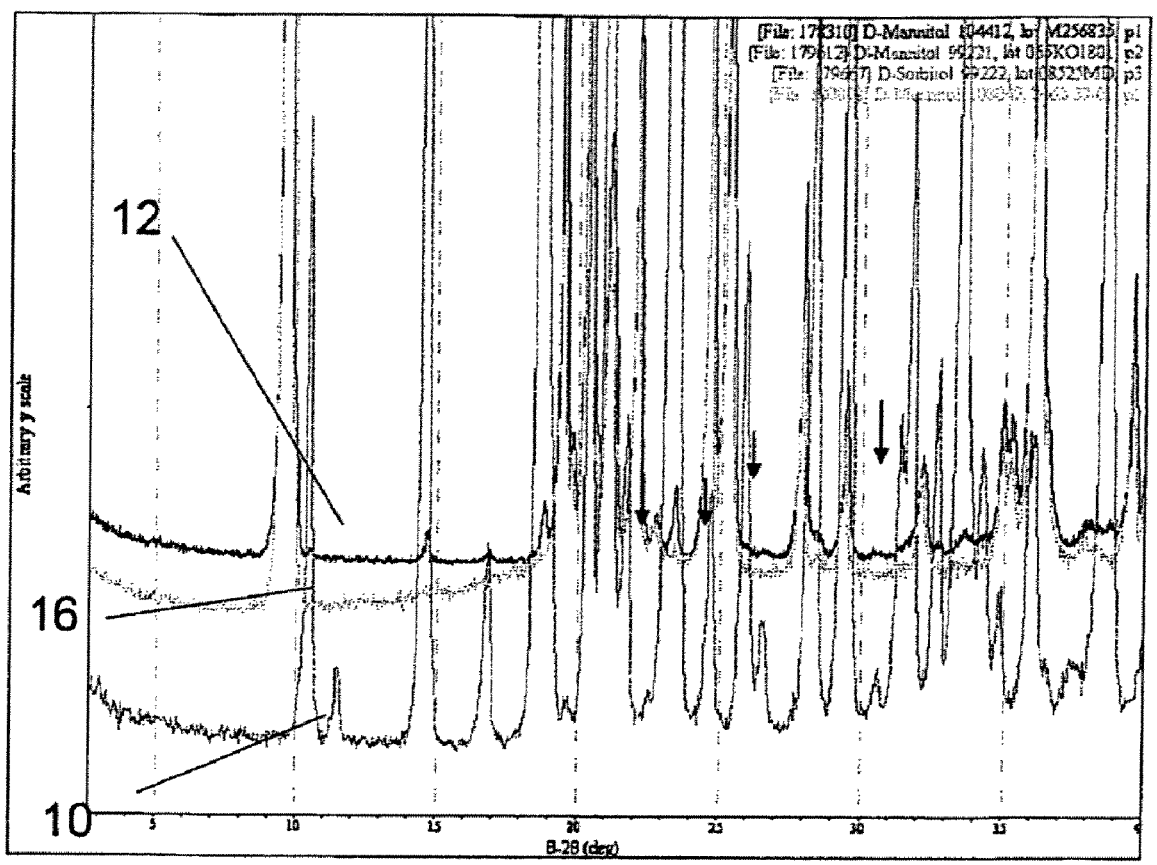
FIG. 2 is an x-ray powder diffraction pattern comparing the diffraction patterns of mannitol modification I, commercially available mannitol modification III and mannitol modification III produced by the method of the present invention with sorbitol as the auxiliary agent.

As illustrated in the x-ray diffraction pattern of FIG. 2, mannitol modification III produced by the methods of the present invention (16) has less of modification I than commercially available modification III (12). The diffraction pattern of modification I (10) is included for comparison. The arrows show where peaks associated with modification I. While these peaks are still present in the diffraction pattern for the commercially available modification III (12) they are not detected for the product formed using the methods of the present invention (16).

The examples set forth below are exemplary only and are not meant to limit the invention to any particular embodiment.

EXAMPLES

Example 1

Material and Methods

All materials used were purchased from commercial suppliers and used as received:

| Compound | Manufacturer/Lot No. |
|---|---|
| D-Mannitol (modification I) | Sigma-Aldrich, 065KO1801 |
| D-Mannitol (modification III) | EM Science, M256835 |
| D-Sorbitol | Aldrich, 08525MD |
| α-D-glucose | Aldrich, 06723AN |
| Glycolic acid | Sigma-Aldrich, 03613LC |
| Citric Acid | Aldrich, KN07010DN |
| D-Fructose | Aldrich, 11208MC |
| D(+)-Mannose | Acros, A017868101 |
| NaCl | Sigma-Aldrich, 026KO117 |
| Xylitol | Sigma, 22KO147 |
| $CaCl_2$ | Fisher, 037206 |
| $KNO_3$ | Sigma-Aldrich, 05911CD |

All crystallizations were performed in a NesLab© RTE-211 cooling bath containing ethylene glycol. Cooling rates of 1° C./min were utilized. All observations during the crystallization process were made via visual inspection.

X-ray powder diffraction (XRPD) analyses were performed using a Shimadzu XRD-6000 X-ray powder diffractometer using Cu Kα radiation. The instrument is equipped with a long fine focus X-ray tube. The tube voltage and amperage were set to kV and 40 mA, respectively. The divergence and scattering slits were set at 1° and the receiving slit was set at 0.15 mm. Diffracted radiation was detected by a NaI scintillation detector. A θ-2θ continuous scan at either 2 or 3°/min (0.04° step or 0.02° step) from 2.5 to 40° 2θ was used. A silicon standard was analyzed to check the instrument alignment. Data were collected and analyzed using XRD-6000 v. 4.1

Tables 1 and 2 summarize each of the examples and the results of those experiments. The table sets forth the concentration of auxiliary agent, the concentration of D-Mannitol, the temperature for dissolution of all solvents ($T_{in}$), the temperature at which mannitol modification III solidified out ($T_{out}$), and the result obtained from analyzing the x-ray powder diffraction pattern of the solidified material from solution.

TABLE 1

Modification III of D-Mannitol - Starting with D-Mannitol/Sorbitol Solutions

| Trial | D-Sorbitol Conc. (g/ML) | D-Mannitol (Form) - (g/mL) | D-Mannitol Loading (g/mL) | Solids Loading (g/mL) | $T_{in}$ (° C.) | $T_{out}$ (° C.) | Result |
|---|---|---|---|---|---|---|---|
| 1 | 1.0 | 0.23 (I) | 0.229 | 1.23 | 45 | 5 (dwell) | I |
| 2 | 0.5 | 0.33 (I) | 0.320 | 0.83 | 45 | 22.7 | I |
| 3 | 0.25 | 0.41 (I) | 0.409 | 0.66 | 50 | 28.7 | III |
| 4 | 0.125 | 0.455 (I) | 0.452 | 0.58 | 58 | 42.9 | I |
| 5 | 0.0625 | 0.468 (I) | 0.467 | 0.53 | 55 | 38.1 | I |

TABLE 1-continued

Modification III of D-Mannitol - Starting with D-Mannitol/Sorbitol Solutions

| Trial | D-Sorbitol Conc. (g/ML) | D-Mannitol (Form) - (g/mL) | D-Mannitol Loading (g/mL) | Solids Loading (g/mL) | $T_{in}$ (°C.) | $T_{out}$ (°C.) | Result |
|---|---|---|---|---|---|---|---|
| 6  | 0.0241 | 0.466 (I)       | 0.466 | 0.49  | 55   | 39   | I |
| 7  | 0.375  | 0.315 (I)       | 0.316 | 0.69  | 45   | 20.4 | III |
| 8  | 0.375  | 0.275 (I)       | 0.277 | 0.65  | 40   | 16.5 | III |
| 9  | 0.375  | 0.235 (I)       | 0.238 | 0.61  | 40   | 9.4  | III |
| 10 | 0.11   | 0.32 (III)      | 0.422 | 0.43  | 57.5 | 41.1 | I |
| 11 | 0.33   | 0.37 (III)      | 0.373 | 0.70  | 57.5 | 39.7 | I |
| 12 | 0.33   | 0.32 (III)      | 0.320 | 0.65  | 50   | 30.9 | III + I |
| 13 | 0.25   | 0.397 (III)     | 0.397 | 0.647 | 57.5 | 39.2 | III + I |
| 14 | 0.25   | 0.30 (III)      | 0.302 | 0.55  | 49   | 27.5 | III + I |
| 15 | 0.325  | 0.325 (III + I) | 0.325 | 0.65  | 44   | 21.3 | III |
| 16 | 0.25   | 0.41 (III)      | 0.405 | 0.66  | 49   | 35.2 | III + I |
| 17 | 0.25   | 0.31 (III)      | 0.31  | 0.56  | 45   | 21.3 | III + I |

TABLE 2

Modification III of D-Mannitol - Starting with Modification I.

| Trial | S.E (Qty-g) | Qty - g | D-Mannitol - g | Solids Loading (g/mL) | $T_{in}$ (°C.) | $T_{out}$ (°C.) | Result |
|---|---|---|---|---|---|---|---|
| 18 | α-D-glucose | 5.13  | 6.31 | 0.572 | 47 | 21.1 | III + I |
| 19 |             | 6.85  | 6.23 | 0.654 | 44 | 21.1 | III + I |
| 20 |             | 7.15  | 6.23 | 0.669 | 44 | 27.6 | III + I + UC |
| 21 | Glycolic acid | 5.03 | 6.34 | 0.569 | 44 | 25.1 | I |
| 22 |             | 7.18  | 6.36 | 0.677 | 44 | 22.2 | I + III |
| 23 |             | 8.42  | 6.40 | 0.741 | 45 | 17.0 | I + III |
| 24 | Citric Acid | 5.00  | 6.34 | 0.567 | 44 | 25.8 | I |
| 25 |             | 7.07  | 6.34 | 0.671 | 44 | 25.9 | I |
| 26 |             | 10.11 | 6.45 | 0.828 | 45 | 16.6 | I |
| 27 | D-Fructose  | 5.05  | 6.30 | 0.568 | 44 | 25.7 | I |
| 28 | D(+)-Mannose | 5.21 | 6.35 | 0.578 | 44 | 24.9 | I |
| 29 | NaCl        | 5.04  | 6.14 | 0.559 | 44 | 15.1 | I |
| 30 |             | 7.11  | 6.37 | 0.674 | 44 | 10.0 (dwell) | I |
| 40 | Xylitol     | 5.15  | 6.37 | 0.576 | 45 | 19.3 | I |
| 41 |             | 6.98  | 6.35 | 0.667 | 45 | 26.8 | I |
| 42 |             | 10.46 | 6.32 | 0.839 | 48 | 28.1 | I |
| 43 | $CaCl_2$    | 5.16  | 6.32 | 0.574 | 45 | 10.0 (dwell) | No solids |
| 44 |             | 15.23 | 6.35 | 1.084 | 45 | 10.0 (dwell) | No solids |
| 45 |             | 31.04 | 6.35 | 1.870 | 45 | 10.0 (dwell) | UC |
| 46 |             | 31.02 | 6.35 | 1.866 | 45 | 10.0 (dwell) | UC |
| 47 | $KNO_3$     | 5.57  | 6.46 | 0.602 | 45 | 12.1 | III + I + UC |
| 48 |             | 4.89  | 6.44 | 0.567 | 45 | 15.8 | I |

UC: unclassified form

Example 2

D-Sorbitol as an Auxiliary Agent

This example corresponds to Trial 8 in Table 1. 7.51 g d-sorbitol was charged into a 50 mL flask containing 20.0 mLs water. The flask was warmed in a 40° C. bath and stirred. Once the solution had clarified (i.e. all solids had gone into solution to the naked eye), 5.53 g d-mannitol was added. A clear solution resulted with stirring. The solution was cooled as described in Example 1. At ~16.5° C., solids appeared in the solution. The sample was vacuum filtered to collect the solids which were then allowed to dry under ambient conditions. A powder x-ray diffraction pattern was collected on the solids and was identified as modification III of mannitol. The results are given in Table 1, Trial 8 and in FIGS. 1 and 2 (16).

Example 3

α-D-Glucose as an Auxiliary Agent

This example corresponds to Trial 19 in Table 2. 6.85 g α-d-glucose was charged into a 50 mL flask containing 20.0 mLs water. 6.23 g d-mannitol of modification I was then added to the flask to form a solution. The flask was warmed in a 44° C. bath and the contents stirred until the solution had clarified. The solution was cooled as described in Example 1 and at about 21.1° C. solids appeared in the solution. The solution was vacuum filtered and the solids were collected and allowed to air dry. X-ray powder diffraction data revealed the solids to be a mixture of modifications I and III of mannitol.

Figure 3:
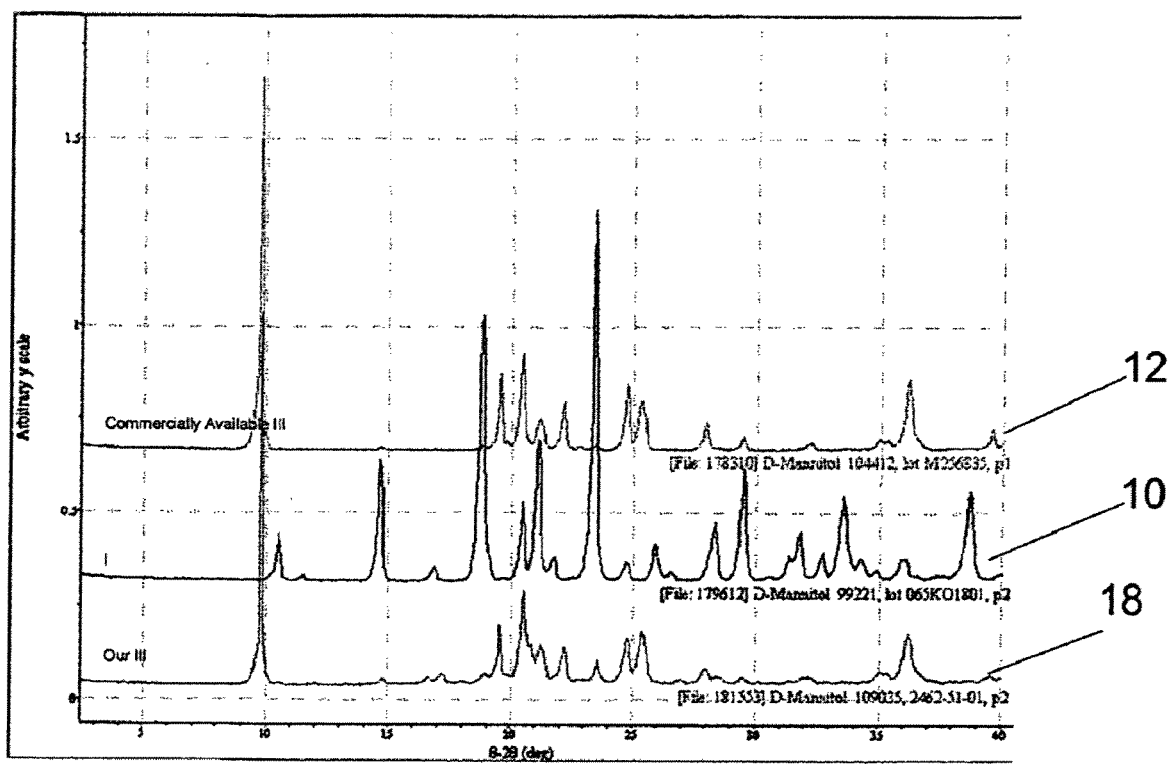
FIG. 3 is an x-ray powder diffraction pattern showing the formation of mannitol modification III from modification I with D-glucose as the auxiliary agent.
Figure 4:
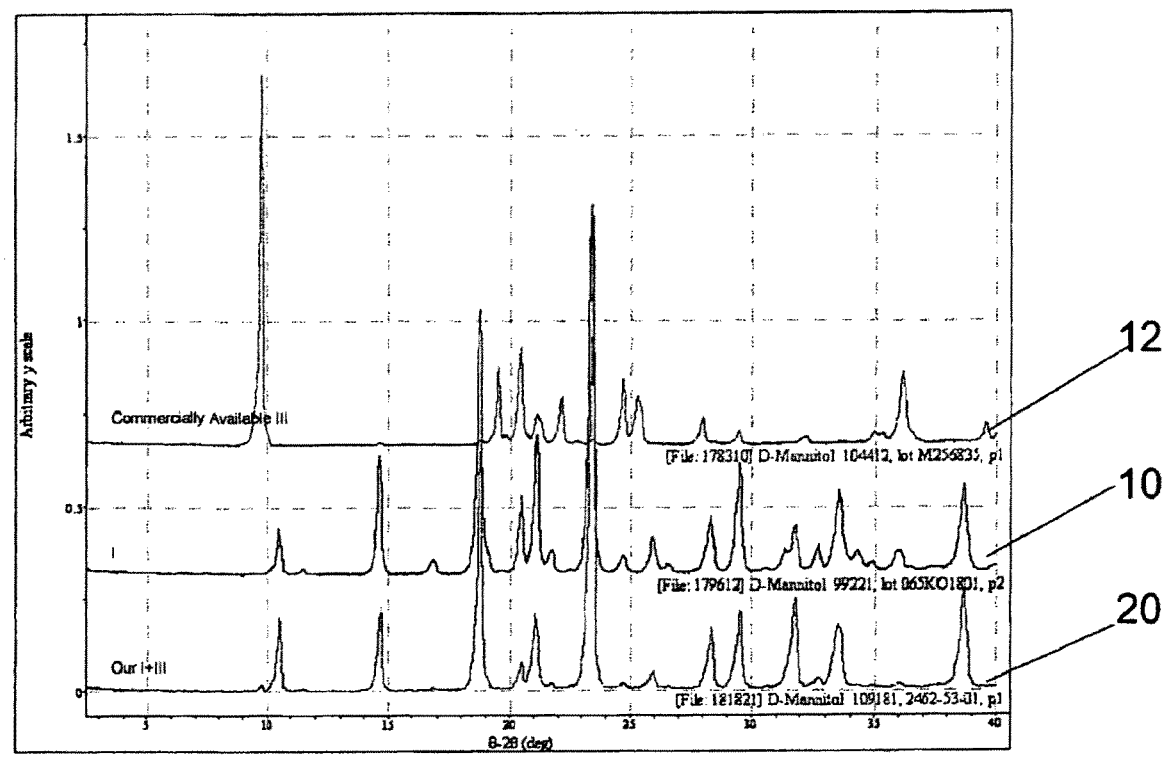
FIG. 4 is an x-ray powder diffraction pattern showing the formation of mannitol modification III from modification I with glycolic acid as the auxiliary agent.

Results from this example are given in Table 2, trials 18-20 and in FIG. 3. The diffraction pattern (18; FIG. 4) shows a product of modification III with about 1% to about 5% of modification I present.

Example 4

Glycolic Acid as an Auxiliary Agent

This example corresponds to Trial 22 in Table 2. 7.18 g glycolic acid was charged into a 50 mL flask containing 20 mLs water. 6.36 g d-mannitol were then added. The flask was warmed in a 44° C. bath and the contents were stirred until the solution clarified. The solution was cooled as described in Example 1 and at ~22.2° C. solids appeared in the solution. The solution was vacuum filtered and the solids were collected and allowed to air dry. X-ray powder diffraction (20, FIG. 4) revealed the solids to be a mixture of modifications I and III of mannitol.

Example 5

Potassium Nitrate as an Auxiliary Agent

Figure 5:
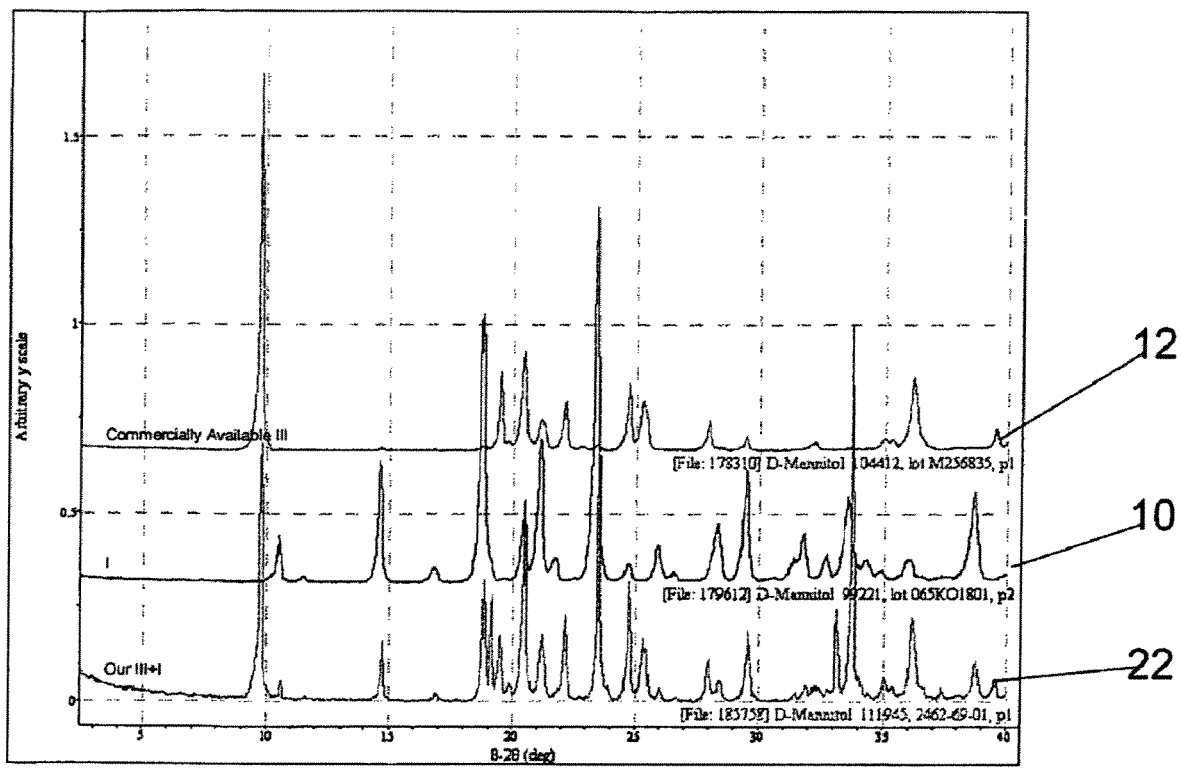
FIG. 5 is an x-ray powder diffraction pattern showing the formation of mannitol modification III from modification I with potassium nitrate as the auxiliary agent.

This example corresponds to Trial 47 in Table 2. 5.57 g potassium nitrate was charged into a 50 mL flask containing 20 mLs water. 6.46 g d-mannitol were then added. The flask was warmed in a 45° C. bath and stirred. Solution clarified. At ~12.1° C. solids appeared in the solution. The solution was vacuum filtered and the solids were collected and allowed to air dry. X-ray powder diffraction revealed the solids to be a mixture of modifications I and III of mannitol (22, FIG. 5).

The claimed invention is:

1. A method for making modification III of mannitol comprising solidifying mannitol modification III from a solution comprising a suitable solvent, mannitol, and an auxiliary agent.

2. The method of claim 1 wherein the suitable solvent is water.

3. The method of claim 1 wherein the auxiliary agent is of greater solubility than the solubility of mannitol modification III in the suitable solvent.

4. The method of claim 1 wherein the auxiliary agent is selected from sorbitol, potassium nitrate, glycolic acid and glucose.

5. The method of claim 1 wherein the mannitol placed into solution is of modification I, II, III, the hemihydrate, an amorphous form, or a combination thereof.

6. The method of claim 1 wherein the solidified mannitol is crystallized.

7. The method of claim 1 wherein the solidified mannitol is solidified by cooling.

8. The method of claim 1 wherein the solidified mannitol is characterized by an x-ray powder diffraction pattern having a peak at about 9.8 degrees two-theta.

9. The method of claim 1 where the auxiliary agent has a concentration of from about 0.25 g/ml to about 0.4 g/ml.

10. A method of producing modification III of mannitol comprising the steps of:
    dissolving an auxiliary agent and mannitol in a solvent to form a solution; and
    solidifying mannitol modification III from the solution.

11. The method of claim 10 further comprising isolating the mannitol modification III solidified from the solution.

12. The method of claim 10 wherein the mannitol added to the solvent is modification I,II, III, the hemihydrate, an amorphous form, or a combination thereof.

13. The method of claim 10 wherein the mannitol and auxiliary agent are added sequentially or simultaneously.

14. The method of claim 10 wherein the auxiliary agent is sorbitol or glucose.

15. The method of claim 10 wherein the mannitol modification III is solidified by cooling the solution.

16. The method of claim 15 wherein the solution is cooled to about 0° C. to about 45° C.

17. The method of claim 10 wherein the mannitol or the auxiliary agent is dissolved into solution by increasing the temperature of the solvent.

18. The method of claim 17 wherein the temperature is raised to from about 40° C. to about 50° C.

* * * * *